United States Patent [19]

Kamen

[11] Patent Number: 5,416,156
[45] Date of Patent: May 16, 1995

[54] SURFACE COATING COMPOSITIONS CONTAINING FIBRILLATED POLYMER

[75] Inventor: Melvin E. Kamen, Highlands, N.J.

[73] Assignee: Revlon Consumer Products Corporation, New York, N.Y.

[21] Appl. No.: 169,279

[22] Filed: Dec. 20, 1993

Related U.S. Application Data

[63] Continuation-in-part of Ser. No. 258,219, Oct. 14, 1988, Pat. No. 4,938,952.

[51] Int. Cl.$^6$ .............................................. C08L 27/00
[52] U.S. Cl. .................................. 524/520; 524/847; 524/407; 524/431; 524/439; 524/441; 524/495; 524/496; 523/206; 523/215
[58] Field of Search ............... 524/520, 847, 407, 431, 524/439, 441, 495, 496; 523/206, 215

[56] References Cited

U.S. PATENT DOCUMENTS

| | | |
|---|---|---|
| 3,714,102 | 2/1973 | Reiss . |
| 3,838,092 | 2/1974 | Vogt . |
| 3,869,430 | 12/1975 | Blades . |
| 4,332,698 | 3/1982 | Bernstein . |
| 4,358,396 | 7/1982 | Bernstein . |
| 4,421,660 | 5/1983 | Solc nee Hajna . |
| 4,433,063 | 7/1984 | Bernstein . |
| 4,510,273 | 7/1985 | Miura . |
| 4,596,839 | 10/1986 | Peters . |
| 4,608,401 | 1/1986 | Martin . |
| 4,665,107 | 4/1987 | Micale . |
| 4,693,749 | 8/1987 | Gale . |
| 4,810,381 | 3/1989 | Hagen et al. ..................... 210/502.1 |
| 4,971,697 | 2/1990 | Douden . |
| 5,068,265 | 11/1991 | Casey et al. ........................ 524/533 |
| 5,093,110 | 11/1992 | Kamen . |
| 5,219,633 | 11/1993 | Sabee . |

OTHER PUBLICATIONS

Chemical Engineering, Jan. 1993 p. 59 "The Perfect Asbestos Substitute".
Paint & Coatings Industry, Aug. 1993, p. 36 "Kevlar Aramid Pulp: The Reinforcing Thixotrope".

*Primary Examiner*—Paul R. Michl
*Assistant Examiner*—Edward Cain
*Attorney, Agent, or Firm*—Julie Blackburn

[57] ABSTRACT

A surface coating composition comprising, in combination, a fibrillated polymer matrix, at least one pigment, at least one binder, and at least one solvent, and a method for the manufacture thereof.

32 Claims, No Drawings

SURFACE COATING COMPOSITIONS CONTAINING FIBRILLATED POLYMER

This application is a continuation-in-part of U.S. Ser. No. 258,219 filed Oct. 14, 1988, now U.S. Pat. No. 4,938,952.

TECHNICAL FIELD

The invention is in the field of pigmented coating compositions such as paint, lacquer, varnish, inks, and the like.

BACKGROUND OF THE INVENTION

Liquid paint is essentially a suspension of finely divided pigment particles in a liquid vehicle composed of a resin or binder and a volatile solvent. After the paint is applied the volatile solvent evaporates from the drying film and the binder holds the pigment in the dry film and causes it to adhere to the substrate.

There are two basic types of paints, referred to as water emulsion based and oil based. Water emulsion based paints, often referred to as latex paints, are composed of suspension of pigment particles and finely divided emulsified synthetic polymers in water. After the paint is applied to the substrate, the water evaporates from the drying film and the particles coalesce into a continuous film which acts as the pigment binder and adheres to the substrate. Oil based paints are composed of a dispersion of pigment particles in an oil based vehicle, such as an alkyd resin, in a solvent of mineral spirits. An alkyd resin is the reaction product of a polybasic acid (such as phthalic acid) and a polyhydric alcohol (for example, glycerol). Alkyds can be produced from a wide variety of polybasic acids, polyhydric alcohols, and monobasic fatty acids available in numerous molecular weight distributions.

In the manufacture of both oil and water based paints, pigments are suspended in the liquid phase of the paint compositions. Many of the pigments used in paints are difficult to disperse and suspend in the liquid phase. Iron oxides, for example, are highly charged particles which tend to agglomerate when suspended in liquids. Some of the other organic pigments used in paints are also difficult to suspend and disperse because of their molecular configuration. It is known to coat or encapsulate pigment particles to modify surface characteristics using certain polymeric materials. This practice is quite expensive, however, and adds a substantial cost to the final product. There remains a need for improved methods of suspending and dispersing pigments in industrial coating compositions such as paints, lacquers, and varnishes.

It is known in the prior art that certain polymers such as polytetrafluoroethylene (PTFE), polypropylene, polyethylene, etc. are capable of fibrillation.

Fibrillated polymers have been used to support various particulates. For example, in U.S. Pat. Nos. 4,938,952 and 5,093,110 to Kamen, fibrillated polymers are used to support cosmetic pigments in cosmetic compositions. U.S. Pat. No. 3,838,092 discloses the use of fibrillated polymers to pelletize solid particulate matter such as dust. U.S. Pat. No. 4,971,697 discloses sorptive silica particles enmeshed in a matrix of fibrillated polymer for use in chromatographic procedures.

It has most unexpectedly been discovered that pigments may be dispersed and suspended quite effectively in industrial coating compositions such as paints, lacquers, and varnishes by embedding the pigment in a fibrillated polymer network.

SUMMARY OF THE INVENTION

The invention is directed to a surface coating composition comprising, in combination, a fibrillated polymer matrix, at least one pigment, at least one binder, and at least one solvent.

The invention is also directed to method for suspending pigments in a surface coating composition comprising, in combination, a fibrillated polymer matrix, at least one pigment, at least one binder, and at least one solvent, by:

a) exposing a mixture of fibrillatable polymer and pigment to high shear whereby the fibrillatable polymer forms a fibrillated polymer matrix and the pigment becomes enmeshed within the matrix, b) incorporating the fibrillated polymer matrix containing enmeshed pigment into the surface coating composition.

DETAILED DESCRIPTION

The term "extender" means a particle having an index of refraction ranging from 1.40 to 1.64 and a specific gravity ranging from 2.0 to 3.0. The particle size of extenders generally ranges from 0.04 microns to 500 microns. Extender particles have very little hiding power or capability of imparting color in their own right, but are included in coating compositions for other useful purposes such as flattening, color dilution, rheology control, or color enhancement. Extenders are usually considered chemically inert. Examples of extenders include barium sulfate pigments such as blanc fixe or ground barytes, calcium carbonate pigments (including limestone and chalk), calcium sulfate pigments such as gypsum, anhydrite, and precipitated calcium sulfate, silicate pigments such as silica, diatomaceous silica, clay, pyrophyllite, talc, mica, phlogopite, and muscovite.

The term "surface coating composition" means coating compositions applied to exterior and interior surfaces of wood, plastic, metal, or paper for protective and/or decorative purposes. Examples of such coating compositions include exterior and interior house paint, varnish, lacquer, automotive paint, enamels, printing ink, etc.

The term "pigment" means a finely divided insoluble particle which imparts color including black or white to paint. In the case of white pigments, this means that the particle has a refractive index ranging from 1.93 to 2.76. Pigments which impart color and thus have hiding power include titanium dioxide (both rutile and anastase), and colored inorganic pigments such as zinc chromates (zinc potassium chromate), Prussian blue, chromium oxide, iron oxides, ultramarine, cadmium, vermilion, cobalt blue, aluminum powder, zinc dust, carbon black, and graphite. Various organic pigments also provide color including anthroquinones, di- and triphenyl methanes, azine, oxazine, xanthene, thioindigoid, phthalocyanine, quinacridone, the Lakes, etc.

The term "finely divided synthetic polymer" means a stable, fine dispersion of synthetic polymer in water, usually obtained by emulsion polymerization of monomers. The finely divided synthetic polymers must be capable of coalescing with evaporation of water, and when incorporated into a coating composition cause binding of the pigment and extender particles to the surface to which the coating composition is applied.

The styrene-butadiene polymers, polyvinyl acetate polymers, latex, and acrylic polymers are most widely used. Other suitable polymers include styrene, butyl acrylate, butadiene, vinylidene chloride, vinyl chloride, ethylene, methyl methacrylate, ethyl acrylate, vinyl acetate, methyl acrylate, and epoxies.

The term "mineral spirits" means a petroleum distillate that distills at 150°-200° C. and which is used as an organic volatile in paints.

The term "alkyd" means a synthetic resin made from fatty acids or fatty oils, polybasic acids, and polyhydric alcohols. Alkyd resins are typically the reaction product of polyhydric alcohols and polybasic acids. Glycerol, pentaerythritol, ethylene glycol, sorbitol, trimethylolethane, trimethylolpropane, dipentaerythritol, tripentaerythritol, neopentyl glycol and diethylene glycol are some of the polyhydric acids used. The polybasic acids are phthalic acid, terephthalic acid, isophthalic acid, maleic acid, fumaric acid, linoleic and oleic acids.

The term "paint" means a liquid composition which, when applied to a substrate, will impart color, including black or white, to the substrate. Included are standard interior and exterior paints, enamels, automotive paints, marine paints, and so on.

The term "fibrillation" or "fibrillated" means the explosion of a polymer into fibrils or minute fibers upon exposure to heat, shear, and/or other pressure. Not all polymers will fibrillate. A polymer which has not yet been fibrillated but is capable of fibrillation is referred to as a "fibrillatable" polymer.

The term "matrix" means an open structured entangled mass of microfibers.

The term "binder" means a resin, finely divided synthetic polymer, or other ingredient which holds the pigments and extenders in the dry coating film and causes adherence of the pigments and extenders to the substrate.

The term "solvent" means water or other nonaqueous solvents such as mineral spirits, alcohol, and the like.

The term "oil-based" means that the liquid or solvent in the coating composition comprises oil or oil miscible substances.

The term "water-based" means that the liquid or solvent in the coating composition comprises water.

Preparation of the Pigment Enmeshed in the Fibrillated Matrix

The preparation of the pigment enmeshed in the fibrillated polymer matrix begins with the selection of a fibrillatable polymer. Suitable fibrillatable polymers must be compatible with and capable of dispersing the pigments which are used; the fibrillatable polymer must be nonreactive with both the pigment and the composition in which the fibrillated polymer matrix is to be incorporated. A number of PTFE polymers are known to be fibrillatable including Teflon 6A and 7A by DuPont which are commercially available as dry powders. Other fluorocarbons and polyolefins are also fibrillatable, such as polyethylene, polypropylene, and copolymers of ethylene with an alpha-olefin such as ethylene/propylene copolymer, ethylene/1-butene copolymer and ethylene/4-methyl-1-pentene copolymer. The characteristics of the final composition containing the pigment enmeshed into the fibrillated matrix can be controlled by the fibrillatable polymer selected. Fibrillatable polymers exhibit varying degrees of inertness, imperviousness, and wettability. For example, PTFE is very inert, hydrophobic and impervious to water and most other solvents. PTFE fibers will not swell or take up liquid from the surrounding environment. Thus, if PTFE is used as the fibrillated polymer matrix, the resulting paints will be very impervious to environmental assaults such as rain, sleet, or dirt. In addition, the inertness of PTFE will decrease the possibility of reaction with ingredients in the surrounding liquid composition. The low wetting angle of PTFE fibers will cause better application of the paint to the substrate and improve breathability of the dried paint film.

The pigment enmeshed within the fibrillated polymer matrix is preferably made in a dry process wherein the pigment and fibrillatable polymer are subjected to high shear in a high shear mixer such as a Blendex Mixer with a blade speed of approximately 12,000-15,000 rpm with a change in temperature or pH (in the case of emulsion fibrillation). Generally the pigment/fibrillatable polymer ratio can range from 1 to 10:10 to 1, however a ratio of approximately 5 to 10:1 to 5 is preferred. The pigment/fibrillatable polymer mixture is then subjected to high shear for a period of time sufficient to cause the polymer to form a fibrillated mass in which the pigment particles are embedded or enmeshed. High shear mixing from 1-15 minutes will be generally be sufficient to cause the desired degree of fibrillation and pigment dispersion. Heat will be generated with high shear and care must be made so that the temperature will not approach the melting point of the polymer being fibrillated.

If desired, the fibrillation step can be carded out in situ. In situ fibrillation means that the polymer is fibrillated in the presence of at least one component of the final coating composition. In this case, the fibrillatable polymer, the pigment, and various other ingredients such as the extender pigments, water, dispersants, surfactants, preservatives, and the like are mixed in a suitable mixer such as a Cowles mixer. The high speed mixing will cause the polymer to fibrillate in situ and the pigment will become enmeshed in the fibrous strands.

Although any fibrillatable polymer may be used, PTFE is preferred, particularly PTFE 6A and 7A by DuPont.

After the pigment enmeshed in the fibrillated polymer matrix is prepared, it is then incorporated into the desired coating composition which includes varnish, water-based or oil-based paint, enamel, lacquer, ink, etc.

The Water Based Pigmented Coating Composition

In water based surface coating compositions such as paints, enamels, and lacquers the solvent is water. The binder is a finely divided synthetic polymer as defined above. The paint compositions of the invention are particularly suitable for application to wood of interior and exterior surfaces. The dispersion of the pigment in the fibrillated polymer provides better application of the paint to the substrate. When the paint is applied to the surface an impervious fibrous network which permits the substrate to "breathe" and reduces the blistering which is commonly found when paint is applied to wooden substrates which contain moisture. The impervious fibrous network also holds the pigment in place, and the fibrillated polymers, particularly Teflon, has a comparatively small wetting angle which causes the paint to repel water, dirt and other substances more effectively.

The preferred formulation of the water-based coating composition comprises:

10–50% water,
5–40% extender,
5–15% finely divided synthetic polymer,
10–40% pigment, and
1–50% fibrillated polymer matrix.

The water-based coating compositions may also contain other ingredients which enhance the properties of the composition, such as dispersants, deflocculants, surfactants, preservatives, thickeners, and the like. Suggested ranges of these ingredients are 0.01–15% dispersant, 0.01–5% defloculant, 0.01–20% surfactant, and 0.01–5% thickener. Any mixture of these additional ingredients may be incorporated into the composition as desired.

The Oil-Based Coating Composition

The fibrillated polymer matrix containing enmeshed pigment is well suited for use in oil-based coating compositions such as paint, lacquer, and the like. Oil-based coating compositions of the following general formula are preferred:
10–30% pigment,
10–50% extender,
5–20% alkyd resin,
20–40% mineral spirits, and
1–50% fibrillater polymer matrix.

The oil-based coating composition may also contain a variety of additional ingredients which enhance the composition's properties. Such ingredients include dispersants, deflocculants, surfactants, preservatives, thickeners, and the like. Suitable ranges are similar to those set forth previously.

Inks

The surface coating composition of the invention includes inks used for decorative or printing purposes. Suitable ink pigments include various inorganic and organic pigments. Organic pigments most often used are the azo and triphenylmethane, anthraquinone, vat, and phthalocyanine dyes. Suitable inorganic pigments include carbon black, titanium dioxide, zinc sulfide, zinc oxide, and mixtures thereof.

A wide variety of binders are used in inks including phenolic resins, alkyds, nitrocellulose, oils, rosins, phthalates, epoxies, polyamides, shellac, etc. Extenders such as alumina hydrate, magnesium carbonate, clacium carbonate, blanc fixe, barium sulfate, and clay are most widely used.

Suitable solvents include alcohols such as ethanol, isopropanol, propanol, propylene, glycol, and the like.

The preferred ink formulation of the invention comprises, by weight of the total composition:
5–50% pigment
2–30% fibrillated polymer matrix
20–50% solvent, and
1–20% binder.

The Method For Suspending Pigments

The invention is also directed to a method for suspending pigments in a surface coating composition. The pigments are fibrillated in accordance with the methods described herein. The fibrillated polymer matrix containing enmeshed pigment is then incorporated into coating compositions such as paint, ink, varnish, enamel, lacquer, and the like by mixing the fibrillated polymer matrix with the paint vehicle. In the alternative, the pigments and fibrillatable polymer can be exposed to the fibrillation step in the presence of at least one other component of the final coating composition so that the fibrillation step occurs in situ.

The invention will be further described in connection with the following examples which are set forth for the purpose of illustration only.

EXAMPLE 1

An inorganic oxide enmeshed in a fibrillated polymer matrix was prepared by blending 9 grams of ultramarine violet-3519 with 1 gram of Teflon 7A (polytetrafluoroethylene or PTFE) for two minutes in an IKA-WERK miniblender at room temperature. During the mixing, the blender was inverted or shaken a number of times to ensure complete mixing of the PTFE with the pigment. The pigment enmeshed in the matrix of PTFE was removed from the blender and stored.

EXAMPLE 2

Titanium dioxide enmeshed in a fibrillated polymer matrix is prepared by blending 10 grams of titanium dioxide with 2 grams of Teflon 7A for two minutes in an IKA-WERK miniblender at room temperature. The blending causes the Teflon to fibrillate and the titanium dioxide to become enmeshed in the fibrillated Teflon matrix.

EXAMPLE 3

An oil based paint containing pigment enmeshed in the fibrillated PTFE matrix of Example 1, is made as follows:

|  | w/w % |
| --- | --- |
| Titanium dioxide* | 14.8 |
| Calcium carbonate | 32.4 |
| Silica and silicates | 11.3 |
| Alkyd resin | 10.0 |
| Mineral spirits | 31.5 |
|  | 100.0 |

*Titanium dioxide enmeshed in fibrillated PTFE

EXAMPLE 4

A water based latex paint containing pigment enmeshed in the fibrillated PTFE matrix of Example 1, is made as follows:

|  | w/w % |
| --- | --- |
| Carboxymethylcellulose 7H3SF (1.5%)[1] | 11.70 |
| Vancide TH preservative[2] | 0.05 |
| Water | 9.20 |
| Ethylene glycol | 2.20 |
| Darvan No. 7 dispersant[3] | 0.90 |
| Antifoamer | 0.35 |
| Ammonium hydroxide (28%) | 0.20 |
| Titanium dioxide[4] | 17.40 |
| Nytal 3000 magnesium silicate[5] | 19.60 |
| Rhoplex AC-33 Acrylic emulsion[6] | 28.00 |
| Veegum T thickener (4% solution)[7] | 8.70 |
| Wetting agent | 1.70 |
|  | 100.00 |

[1]Hercules, Inc.
[2]liquid hexahydro-1,3,5-triethyl-s-triazine preservative, R. T. Vanderbilt & Co.
[3]polyelectrolyte dispersing agent (25% solids in water), R. T. Vanderbilt Co.
[4]titanium dioiude enmeshed within fibrillated PTFE matrix
[5]magnesium silicate talc pigment, R. T. Vanderbilt & Co.
[6]acrylic emulsion, 46.5% solids, Rohm and Haas Co.
[7]colloidal magnesium aluminum silicate thickener, R. T. Vanderbilt & Co.

EXAMPLE 5

A blue paint suitable for interior and exterior surfaces was made as follows:

|  | w/w % |
|---|---|
| Propylene glycol | 7.83 |
| Water | 27.90 |
| Colloid 111 Dispersant[1] | 0.72 |
| AW-95 dispersant[2] | 0.27 |
| Natrosol 250HR thickener[3] | 0.27 |
| Colloid 643 defoamer[4] | 0.31 |
| Dowicil 75 preservative[5] | 0.09 |
| Titanium dioxide[6] | 22.64 |
| Butyl cerosolve solvent[7] | 2.40 |
| Colloid 643 defoamer[8] | 0.18 |
| Amsco Res 3016 vinyl acetate-acrylic copolymer emulsion[9] | 36.22 |
| Igepal CO-610 surfactant[10] | 0.18 |
| Triton GR-7M surfactant[11] | 0.18 |
| Cal tint blue colorant[12] | 10.00 |
|  | 100.00 |

[1] anionic dispersant and deflocculant for titanium dioxide (25% solution in water), Colloids, Inc.
[2] 2-amino-2-methyl-1-propanol with 5% water, International Minerals & Chemical Corp.
[3] water soluble hydroxyethylcellulose ether thickener, Hercules, Inc.
[4] Colloids, Inc.
[5] 1-(3-chloroallyl)-3,5,7-triaza-1-azoniaadamantane chloride, Dow Chemical USA
[6] enmeshed within a fibrillated PTFE matrix
[7] ethylene glycol monobutyl ether, Union Carbide
[8] Colloids, Inc.
[9] vinyl acetate-acrylic copolymer resin emulsion, Union Chemicals Division
[10] nonionic nonylphenoxypoly(ethyleneoxy)ethanol surfactant (100% active) with 7-8 moles of ethylene oxide, GAF Corp.
[11] dioctyl sodium sulfosuccinate (64% active), Rohm and Haas Co.
[12] enmeshed within a fibrillated PTFE matrix The propylene glycol, approximately one half of the water, Colloid 111, AMP-95 dispersant, Natrosol, Colloid 643 defoamer, Dowicil 75, and titanium dioxide where mixed in a high speed mixer to disperse the pigment. Then, at slow speed the remaining ingredients were added.

What is claimed is:

1. A liquid surface coating composition selected from the group consisting of paint, varnish, enamel, lacquer, and printing ink comprising, in combination, at least one binder, at least one solvent, and a fibrillated polymer matrix having at least one pigment enmeshed within said matrix.

2. The composition of claim 1 wherein the fibrillated polymer matrix is made from a fibrillatable polymer which is exposed to heat, shear, or pressure.

3. The composition of claim 2 wherein the polymer in the fibrillated polymer matrix is a fluorocarbon or polyolefin.

4. The composition of claim 3 wherein the polymer is selected from the group consisting of PTFE, polyethylene, polypropylene, ethylene/propylene copolymer, ethylene/1-butene copolymer, ethylene/4-methyl-1-pentene copolymer, and mixtures thereof.

5. The composition of claim 4 wherein the polymer is PTFE.

6. The composition of claim 2 wherein the surface coating composition is an anhydrous oil-based paint or a water-based paint.

7. The composition of claim 6 wherein the surface coating comosition is a water-based paint.

8. The composition of claim 7 wherein the solvent is water.

9. The composition of claim 8 wherein the binder is a finely divided synthetic polymer.

10. The composition of claim 9 wherein the finely divided synthetic polymer is selected from the group consisting of latex, styrene-butadiene, polyvinyl acetate, acrylic polymer, styrene butyl acetate, butadiene, vinylidene chloride, vinyl chloride, ethylene methacrylate, ethyl acrylate, vinyl acetate, methyl acrylate, acrylonitrile, and mixtures thereof.

11. The composition of claim 10 further comprising an extender.

12. The composition of claim 11 wherein the pigment is a finely divided insoluble particle having a refractive index of 1.93 to 2.76.

13. The composition of claim 12 wherein the pigment comprises titanium dioxide.

14. The composition of claim 12 wherein the pigment is selected from the group consisting of a colored inorganic pigment and a colored organic pigment.

15. The composition of claim 14 wherein the pigment is a colored inorganic pigment.

16. The composition of claim 14 wherein the extender is a particle of 0.04-500 microns in diameter having a refractive index of 1.40 to 1.64.

17. The composition of claim 16 comprising, by weight of the total composition:
10-50% water,
5-40% extender,
5-15% finely divided synthetic polymer,
10-40% pigment, and
1-50% fibrillated polymer matrix.

18. The composition of claim 17 wherein the fibrillated polymer matrix is PTFE.

19. The composition of claim 2 wherein the surface coating composition is an oil-based paint.

20. The composition of claim 19 wherein the binder is an alkyd resin.

21. The composition of claim 20 wherein the solvent is mineral spirits.

22. The composition of claim 21 comprising an extender.

23. The composition of claim 22 wherein the pigment is a finely divided insoluble particle having a refractive index of 1.93 to 2.76.

24. The composition of claim 23 wherein the extender is a particle of 0.04-500 microns in diameter having a refractive index of 1.40 to 1.64.

25. The composition of claim 24 comprising a pigment selected from the group consisting of a colored inorganic pigment, a colored organic pigment, or mixtures thereof.

26. The composition of claim 25 comprising:
10-30% pigment,
10-50% extender,
5-20% alkyd resin,
20-40% mineral spirits, and
1-50% fibrillated polymer matrix.

27. The composition of claim 26 wherein the fibrillated polymer matrix is PTFE.

28. The composition of claim 27 wherein the pigment is selected from the group consisting of titanium dioxide, zinc chromate, Prussian blue, chromium oxide, iron oxide, ultramarine, cadmium, vermilion, cobalt blue, aluminum powder, zinc dust, carbon black, graphite, anthroquinones, diphenylmethanes, tripheylmethanes, azine oxazine, zanthene, thioindigoid, the Lakes, phthalocyanine, quinacridone, and mixtures thereof.

29. The composition of claim 2 wherein the surface coating composition is an ink.

30. A method for suspending pigments in a pigmented surface coating composition selected from the group consisting of paint, varnish, enamel, lacquer, and printing ink comprising, in combination, at least one binder, at least one solvent, and a fibrillated polymer matrix having at least one pigment enmeshed within said matrix, by:

a) exposing a mixture of fibrillatable polymer and pigment to high shear whereby the fibrillatable polymer forms a fibrillated polymer matrix and the pigment becomes enmeshed within the matrix, b) incorporating the fibrillated polymer matrix containing enmeshed pigment into the surface coating composition.

31. The method of claim 30 wherein the fibrillated polymer matrix is a fluorocarbon or polyolefin.

32. The method of claim 31 wherein the fibrillated polymer matrix is selected from the group consisting of PTFE, polyethylene, polypropylene, ethylene/propylene copolymer, ethylene/1-butene copolymer, ethylene/4-methyl-1-pentene copolymer, and mixtures thereof.

* * * * *